(12) United States Patent
Sharp

(10) Patent No.: US 6,315,760 B1
(45) Date of Patent: Nov. 13, 2001

(54) SYRINGE WITH A BACKGROUND FOR WRITING AND READING INDEX MARKINGS

(75) Inventor: Fraser R. Sharp, Vancouver (CA)

(73) Assignee: Inviro Medical Devices Ltd., Barbados (KN)

( * ) Notice: Subject to any disclaimer, the term of this patent is extended or adjusted under 35 U.S.C. 154(b) by 0 days.

(21) Appl. No.: 09/567,770

(22) Filed: May 9, 2000

(51) Int. Cl.$^7$ ........................................................ A61M 5/00
(52) U.S. Cl. .................................................................. 604/189
(58) Field of Search ............................................. 604/189, 187, 604/218, 219, 220, 221, 222, 223–243

(56) References Cited

U.S. PATENT DOCUMENTS

| | | |
|---|---|---|
| 182,192 | 9/1876 | Hicks et al. . |
| 330,621 | 11/1885 | Reichardt . |
| 332,920 | 12/1885 | Guilbert-Martin . |
| 349,271 | 9/1886 | Crossley et al. . |
| 431,132 | 7/1890 | Wharton . |
| 485,451 | 11/1892 | Carleton . |
| 827,383 | 7/1906 | McElroy et al. . |
| 994,482 | 6/1911 | Schneider . |
| 1,095,313 | 5/1914 | Davids . |
| 1,131,692 | 3/1915 | Gardner . |
| 1,136,108 | 4/1915 | Curtis . |
| 1,232,574 | 7/1917 | Lee . |
| 1,564,048 | 12/1925 | Cook . |
| 1,597,608 | 8/1926 | Ligotz . |
| 2,283,915 | 5/1942 | Cole . |
| 2,303,154 | 11/1942 | Armstrong . |
| 2,586,581 | 2/1952 | Tschischeck . |
| 2,888,015 | 5/1959 | Hunt . |
| 3,512,862 | 5/1970 | Yin . |
| 3,521,366 | 7/1970 | Sampson et al. . |
| 3,690,312 | 9/1972 | Leibinsohn . |
| 3,694,090 | 9/1972 | Ohyama . |
| 3,727,242 | 4/1973 | Miller . |
| 3,774,603 | 11/1973 | McPhee . |
| 3,885,562 | 5/1975 | Lampkin . |
| 4,178,071 | 12/1979 | Asbell . |
| 4,452,251 | 6/1984 | Heilman . |
| 4,724,508 | 2/1988 | Macy . |
| 4,743,121 | 5/1988 | Takagi et al. . |
| 5,062,828 | 11/1991 | Waltz . |
| 5,242,405 | * 9/1993 | Howe ...................................... 604/189 |

FOREIGN PATENT DOCUMENTS

| | | |
|---|---|---|
| 403415 | 11/1910 | (FR) . |
| 21562 | 12/1911 | (GB) . |
| 980805 | 1/1965 | (GB) . |

* cited by examiner

*Primary Examiner*—Manuel Mendez
(74) *Attorney, Agent, or Firm*—Nixon & Vanderhye

(57) ABSTRACT

A syringe includes a barrel having a cannula at one end and a plunger at its opposite end whereby fluid may be drawn into or expressed from the barrel by translatory movement of the plunger relative to the barrel. A white ink receptor coating is provided on the barrel at manufacture and on which coating writing may be applied by the medical practitioner using a common ordinary writing implement such as a ballpoint pen. By locating the ink receptor coating diametrically opposite the index markings on the syringe barrel and providing the coating in a white color, the index markings may be readily read against the contrasting white background to ascertain the quantity of fluid within the syringe barrel.

7 Claims, 2 Drawing Sheets

FIG. 3
FIG. 4
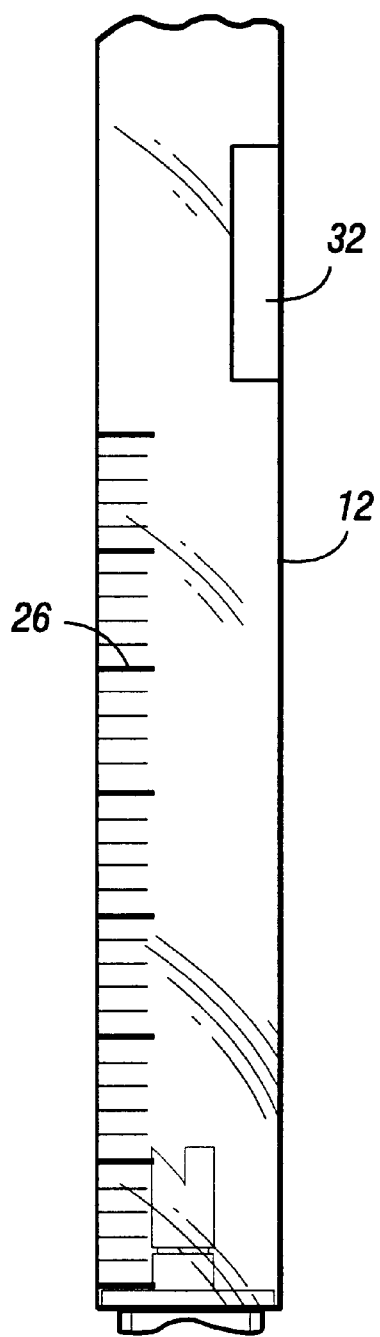
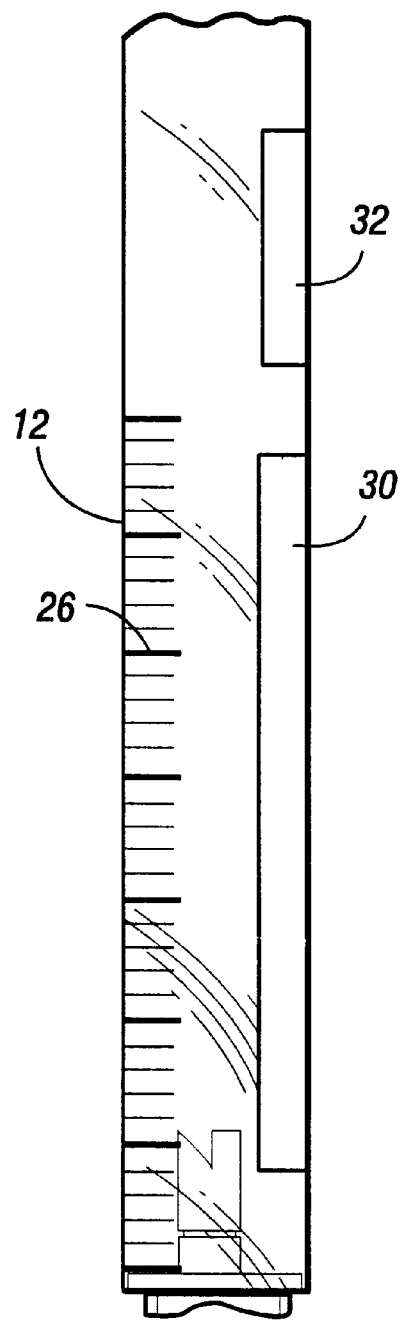

SYRINGE WITH A BACKGROUND FOR WRITING AND READING INDEX MARKINGS

TECHNICAL FIELD

The present invention relates to a syringe for drawing fluid into or expressing fluid from a barrel wherein the barrel has a coating forming a background enabling writing to be applied directly to the barrel using common ordinary writing instruments and facilitating reading the index markings on the barrel.

BACKGROUND

As well known, particularly in the medical field, a syringe comprises an elongated barrel typically formed of transparent material and having a cannula, e.g., a metal or plastic needle, adjacent one end for transmission of fluid into and out of the syringe barrel and a plunger disposed in the barrel and extending through its opposite end. By translating the plunger relative to the barrel, fluid may be drawn into the barrel, for example, from a medication vial or from a patient when drawing blood, or fluid may be expressed from the barrel through the cannula into another medical device or a patient. The barrel of the syringe typically has index markings along one side. The index markings serve to indicate the quantity of fluid within the barrel.

It is not uncommon in medical practice, particularly in an emergency room, operating room or intensive care unit, for patients to be simultaneously receiving a number of different drugs for treatment in an acute situation. Those drugs could include painkillers, psychotropic drugs, heart medications, medications to influence blood pressure, respiration or other physiological aspects. In the acute care situation, these drugs are frequently titrated according to the patient's needs. That is, sequential aliquots of medication are given, often intravenously, through an IV line. The effects are monitored and additional medication given within a short time period if the desired effect is not achieved.

Consequently, there frequently are a number of medical syringes containing different medications all "in use" close to the patient's bedside. Currently, there is no easy method of identifying or making these syringes with useful information, e.g., relating them to their content or to a particular patient, or both. In certain circumstances, indelible marking pens which are not commonplace and are expensive are used to write on the plastic. Alternatively, medical practitioners sometimes apply strips of white tape to the syringe to enable writing to be placed on the strip thereby providing the needed information such as an identification of the medication or the patient, or both or other information. Current syringes are therefore not readily receptive to writing with common ordinary writing instruments and additional measures are typically implemented, for example, applying tape to the syringe barrel to permit writing on the syringes.

Further, while the index markings on a syringe are typically black and may be read against the backgrounds seen through the transparent plastic material forming the syringe barrel, reading the index markings and the level of fluid in the syringe barrel is sometimes difficult, particularly against dark environmental backgrounds. It is therefore difficult with certain background environments to ascertain the quantity of the fluid in the syringe. Accordingly, there is a need for a medical syringe on which writing may be easily applied using ordinary and common writing instruments such as readily available ballpoint pens without the application of ancillary materials to the syringes, as well as a syringe which will facilitate the reading of the index markings on the barrel and hence the quantity of fluid in the barrel.

DISCLOSURE OF THE INVENTION

In accordance with a preferred embodiment of the present invention, a colored coating is applied to the syringe barrel during manufacture of the barrel and therefore forms an integral part of the syringe barrel. The colored coating is preferably a white UV-cured ink-receptive coating applied to the external surface of the barrel in the form of a strip, for example, by a silkscreening process during manufacture. The strip may be applied along the barrel at any location and has a quality and sufficient extent to permit writing to be applied directly to the strip using common writing implements, for example, to identify the fluid within the barrel, a patient, a time for using the syringe, or the like. Particularly, the ink-receptive coating can be applied adjacent the plunger end of the barrel, about the entire circumference of the barrel except where index markings are applied or only partially about the entire circumference of the barrel. This affords sufficient writing area on which the medical practitioner may write using a common writing instrument, such as a ballpoint pen, to provide the necessary information. Alternatively or additionally, the ink-receptive coating may be applied in the form of an elongated strip along the side of the barrel diametrically opposite the index markings. In this form, it will be appreciated that the white strip has a length greater than its width and extends a distance about the barrel approximately one-half of the barrel's circumference. Thus, depending upon the size of the syringe, two or three lines of writing can be applied directly to the integrally formed strip.

The application of a white ink-receptive strip on the side of the barrel opposite the index markings also has other significant beneficial advantages. The placement of the strip opposite the index markings facilitates reading those markings by providing a contrasting background against which the markings are read. Thus, the index markings which are typically black and the fluid level may be read against a background, preferably white in color, thereby affording a significant improvement in the ability to read the index markings. It will also be appreciated that the nature of the coating is consistent with the requirement for a biocompatible, non-toxic compound on a medical syringe.

In a preferred embodiment according to the present invention, there is provided a syringe comprising an elongated syringe barrel formed of a transparent material, a cannula adjacent one end of the barrel for transmission of fluid into or out of the barrel, a plunger disposed in the barrel and extending through an opposite end of the barrel from one end, index markings along one side of the barrel and a colored coating along is another side of the barrel opposite one side and integrally formed on the barrel, the colored coating forming a background contrasting with the index markings to facilitate reading the index markings from one side of the barrel against the contrasting background.

In a further preferred embodiment according to the present invention, there is provided a syringe comprising an elongated syringe barrel formed of a transparent plastic material, a cannula adjacent one end of the barrel for transmission of fluid into or out of the barrel, a plunger disposed in the barrel and extending through an opposite end of the barrel from one end, index markings along one side of the barrel, an ink-receptive colored coating along a side of the barrel, integrally formed on an external surface of the barrel, and contrasting with the transparent plastic material, the coating being receptive to inks enabling writing on the coating on the barrel.

BRIEF DESCRIPTION OF THE DRAWING

FIG. 3 is a view similar to FIG. 2 illustrating the coating located adjacent the fingerpress end of the barrel; and FIG. 4 is a view similar to FIG. 3 illustrating a pair of discrete coatings applied to the barrel at discrete locations.

BEST MODE FOR CARRYING OUT THE INVENTION

Figure 1:
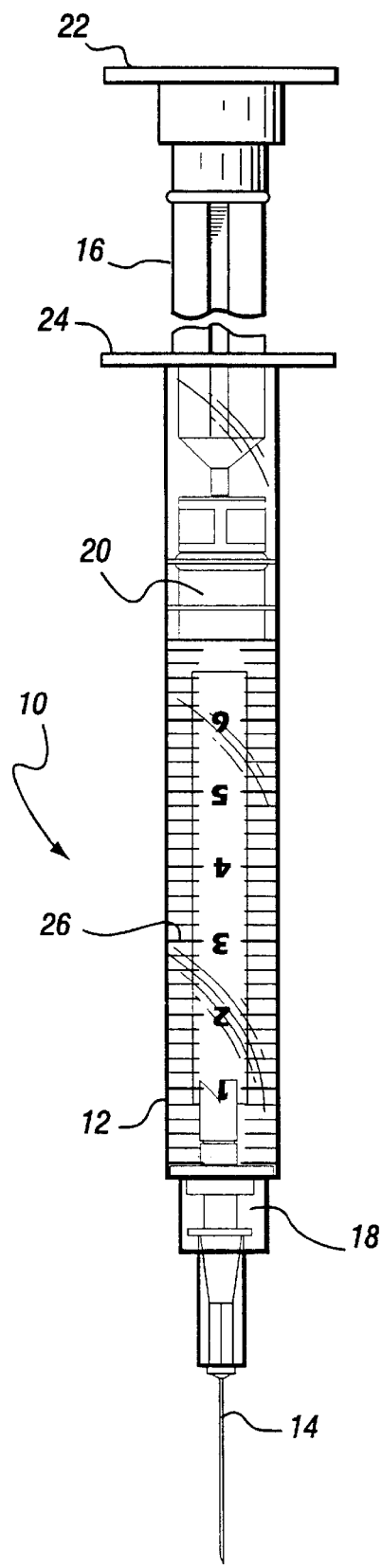
FIG. 1 is a side elevational view with parts broken out for ease of illustration of a medical syringe constructed in accordance with a preferred embodiment of the present invention.

Referring now to the drawings, particularly to FIG. 1, there is illustrated a medical syringe, generally designated 10, including a syringe barrel 12, a cannula 14 and a plunger 16. The syringe 10 may comprise a syringe of any conventional construction but preferably comprises a syringe constructed in accordance with U.S. Pat. No. 6,033,386, the disclosure of which is incorporated herein by reference. In the construction of the syringe of that patent, the cannula 14 may have a Luer fit or be integral with an adapter 18 screwthreaded into the distal end of the barrel. Cooperating engagement structures on the adapter 18 and the distal end 20 of the plunger enable the plunger to engage the adapter, unscrew the adapter and attached cannula from the distal end of the barrel, withdraw the cannula 14 and adapter 18 into the barrel and to seal the barrel ends to prevent needlestick injuries and the escape of fluids from the barrel.

It will be appreciated that in the typical syringe, the proximal end of the plunger 16 includes a thumbpress 22 for translating the plunger 16 in cooperation with a fingerpress 24 on the proximal end of the barrel, into the barrel to express fluid from the barrel through the cannula 14 and facilitating withdrawal of the plunger 16 from the barrel to draw fluid through the cannula 14 into the barrel. It will also be appreciated that the cannula 14 may comprise a standard steel needle or a plastic needle. Conventionally, the barrel is formed of a transparent material, for example, a polyethylene plastic material. Because the barrel is formed of a plastic material, it is difficult to write on such material in the first instance using common writing implements and to retain the ink on the barrel without smudging or smearing. For that reason, the medical practitioner typically applies adhesive tape on the syringe barrel so that information can be recorded, i.e., written on the barrel.

Index markings 26 are also typically applied along the length of the barrel, as indicated in FIG. 1. When read against a background and the fluid level within the syringe barrel, the index markings 26 serve to identify the quantity of fluid within the barrel. It will be appreciated that in the conventional syringe, the index markings are typically formed of a black color and the environment seen through the transparent body of the barrel forms the background against which the index gradations and fluid level are read.

Figure 2:
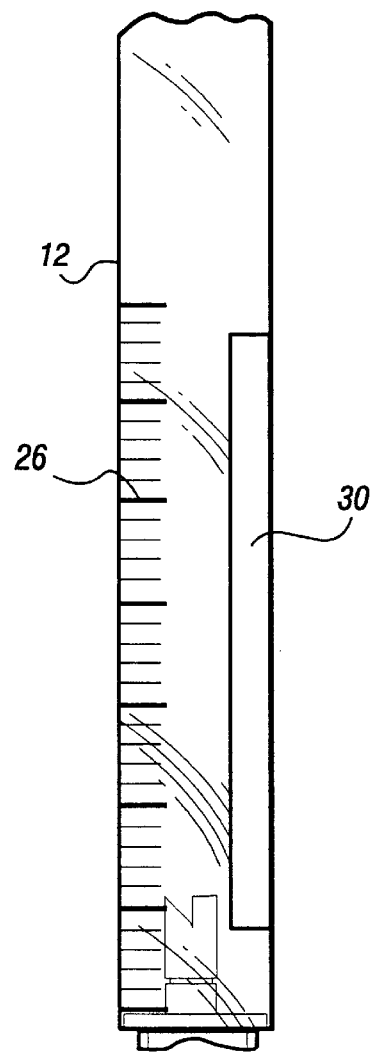
FIG. 2 is a fragmentary enlarged side elevational view of the barrel portion of the syringe of FIG. 1 illustrating the coating and index markings on the syringe barrel.

To provide a syringe on which writing may be applied by a common conventional writing instrument such as a ballpoint pen, typically readily available and commonly used, and to avoid the necessity of applying ancillary material, such as white tape, at the time of usage, the present invention provides a coating on the transparent barrel on which writing may be readily applied by such common writing instrument. Thus, a coating 30 formed of an ink-receptive UV-cured, preferably white, ink is applied along the barrel upon manufacture of the syringe whereby the syringe supplied to the end user, e.g., a medical practitioner, has the coating applied, rendering the barrel readily receptive to writing applied using a common writing implement. The ink may be of the type manufactured and sold by Colorcon, West Point, Pa., under its NO-TOX product line, e.g., NT12 white ink, and with a matting agent, such as silicate (a clay-like material) to enable ink receptivity by common writing instruments such as ballpoint pens, felt tip markers and the like. Another ink for this purpose is manufactured and sold by Coates Screen, Inc., St. Charles, Ill., under the trade identification CDR-TH01. As illustrated in FIG. 2, the coating 30 may be applied in a strip form along the length of the barrel, the length of the strip being in excess of the width of the strip. In FIG. 2, the strip 30 is applied on a side of the barrel diametrically opposite index markings 26 and thus extends about the barrel a distance approximately and typically no greater than one-half the circumference of the barrel. By extending the coating along the length of the barrel substantially coextensive with the index markings, and with the coating having a width approximately one-half the circumference of the barrel, an area is provided on which two or three lines of writing may be readily applied, for example, to identify the medication, the patient, the time of use of the medication and/or other necessary or desirable information.

In FIG. 3, the coating is applied adjacent the fingerpress end of the barrel in a relatively short strip 32 about the barrel and which strip 32 has a length less than the width of the coating. The strip 32 may also be applied completely about the proximal end of the barrel adjacent the fingerpress 24 and extend from the fingerpress 24 to a location adjacent the index markings 26. In FIG. 4, the coatings 30 and 32 may be applied in the form of discrete strips along the side of the barrel opposite the index markings 26. In a still further alternative, the coating may be applied in strip form along the entire length of the barrel, preferably along only one side of the barrel opposite the index markings. Any one of these strips, therefore, provides a background on which a conventional writing instrument may be used to write directly on the syringe supplying necessary or desirable medical information useful to the medical practitioner without the necessity to apply ancillary tapes or take other measures to enable writing to be applied to the syringe.

An additional feature of the present invention enables or facilitates improved reading of the index markings. In this aspect of the present invention, the coating is applied diametrically opposite the index markings 26 to provide a contrasting background within the syringe itself against which the index markings, which are typically black in color, may be readily and easily read. Preferably, the ink coating, e.g., 30 and/or 32, on which writing may be applied is also formulated with a white ink. Consequently, not only does the white ink coating enable writing to be applied to the syringe using ordinary, common, readily available writing instruments, such as ballpoint pens, but the white coating also serves as a sharp contrasting background integral with the syringe against which the index markings 26 may be read. With reference to FIG. 2, it will be appreciated that the coating 30 lies diametrically opposite the index markings 26. Thus, with the syringe inverted in the usual fashion, the quantity of fluid within the barrel can be readily and easily read using the index markings against the contrasting white background. While a white coating is preferred, other colors, preferably light colors, may be used.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A syringe comprising:

an elongated syringe barrel formed of a transparent material;

a cannula adjacent one end of said barrel for transmission of fluid into or out of said barrel;

a plunger disposed in said barrel and extending through an opposite end of said barrel from said one end;

index markings along one side of said barrel; and a colored ink coating having a matting agent along another side of the barrel opposite said one side and integrally formed on said barrel, said colored coating forming a background contrasting with said index markings to facilitate reading the index markings from said one side of said barrel against said contrasting background, said ink coating being ink-receptive to enable writing thereon by a writing instrument.

2. A syringe according to claim 1 wherein said colored coating is white.

3. A syringe according to claim 1 wherein said colored coating comprises a strip thereof along said opposite side of said barrel having a length greater than its width.

4. A syringe according to claim 3 wherein said colored coating comprises a strip extending along said opposite barrel side in the direction of a long axis of the barrel and having a chordal width less than the interior diameter of said barrel.

5. A syringe according to claim 4 wherein the length of said coating strip along said opposite barrel side is substantially coextensive with the length of said index markings along said one side of said barrel.

6. A syringe according to claim 5 wherein said colored coating comprises a white ink-receptive U-V cured coating enabling writing to be applied to said opposite side of said barrel.

7. A syringe according to claim 1 wherein said ink is UV-cured.

* * * * *